(12) United States Patent
Tsao

(10) Patent No.: US 7,935,089 B2
(45) Date of Patent: May 3, 2011

(54) SILICON BREAST IMPLANT INJECTOR FOR AUGMENTATION MAMMAPLASTY

(76) Inventor: Su-Ben Tsao, Kaohsiung (TW)

( * ) Notice: Subject to any disclaimer, the term of this patent is extended or adjusted under 35 U.S.C. 154(b) by 346 days.

(21) Appl. No.: 12/006,986

(22) Filed: Jan. 8, 2008

(65) Prior Publication Data
US 2009/0177165 A1 Jul. 9, 2009

(51) Int. Cl.
A61M 5/315 (2006.01)
A61M 5/00 (2006.01)
A61M 31/00 (2006.01)
A61F 2/12 (2006.01)

(52) U.S. Cl. ............ 604/239; 604/218; 604/60; 623/8

(58) Field of Classification Search ............ 623/8, 7, 623/6.12; 128/898; 606/108; 604/15, 68, 604/27, 57–61, 218, 36, 38, 187, 181–182, 604/219, 228, 239, 264
See application file for complete search history.

(56) References Cited

U.S. PATENT DOCUMENTS

| | | | | |
|---|---|---|---|---|
| 2,323,159 A * | 6/1943 | Smith | ............................. | 604/91 |
| 2,754,822 A * | 7/1956 | Emelock | ............................. | 604/59 |
| 3,212,685 A * | 10/1965 | Swan et al. | ............................. | 222/386 |
| 4,402,308 A * | 9/1983 | Scott | ............................. | 600/7 |
| 4,906,231 A * | 3/1990 | Young | ............................. | 604/110 |
| 4,941,873 A * | 7/1990 | Fischer | ............................. | 604/514 |
| 4,955,906 A | 9/1990 | Coggins et al. | | |
| 5,201,779 A | 4/1993 | Shiao | | |
| 5,232,457 A * | 8/1993 | Grim | ............................. | 604/195 |
| 5,634,903 A * | 6/1997 | Kurose et al. | ............................. | 604/110 |
| 5,792,099 A * | 8/1998 | DeCamp et al. | ............................. | 604/506 |
| 5,827,235 A * | 10/1998 | Beaver | ............................. | 604/236 |
| 6,645,179 B1 * | 11/2003 | Ishikawa et al. | ............................. | 604/181 |
| 6,692,463 B1 * | 2/2004 | Marteau et al. | ............................. | 604/110 |
| 7,137,995 B2 | 11/2006 | Studin | | |
| 2002/0107487 A1 * | 8/2002 | Preuthun | ............................. | 604/218 |
| 2005/0055093 A1 * | 3/2005 | Brennan | ............................. | 623/8 |
| 2006/0161253 A1 * | 7/2006 | Lesh | ............................. | 623/8 |
| 2006/0167419 A1 * | 7/2006 | Fiechter et al. | ............................. | 604/181 |
| 2006/0175348 A1 * | 8/2006 | Wood | ............................. | 222/94 |
| 2006/0184100 A1 * | 8/2006 | Studin | ............................. | 604/59 |
| 2006/0224144 A1 * | 10/2006 | Lee | ............................. | 604/542 |
| 2007/0287965 A1 * | 12/2007 | Strong et al. | ............................. | 604/218 |
| 2008/0269687 A1 * | 10/2008 | Chong et al. | ............................. | 604/180 |
| 2010/0249696 A1 * | 9/2010 | Bardy | ............................. | 604/60 |

* cited by examiner

Primary Examiner — Corrine McDermott
Assistant Examiner — Cheryl Miller
(74) Attorney, Agent, or Firm — WPAT, P.C.; Anthony King

(57) ABSTRACT

A silicon breast implant injector for augmentation mammaplasty which includes a hollow tube and a plunger. The hollow tube has a barrel which has one end tapered to form a first arched barrel connecting to an inverse second arched barrel which in turn is connected to an ejection opening formed at the same diameter as the second arched barrel but into a short inflexible length tube. The plunger can push a silicon breast implant s held in the hollow tube through an incision into patient's submammary pocket. Coupled with a smooth connection between the first arched barrel and the second arched barrel, push resistance can be reduced, and thus can smoothly, quickly, easily and safely move the silicon breast implant into the submammary pocket.

5 Claims, 12 Drawing Sheets

SILICON BREAST IMPLANT INJECTOR FOR AUGMENTATION MAMMAPLASTY

FIELD OF THE INVENTION

The present invention relates to a silicon breast implant injector for augmentation mammaplasty, particularly to an injector to easily and safely insert a silicon breast implant into the submammary pocket to facilitate augmentation mammaplasty and enhance implant safety.

BACKGROUND OF THE INVENTION

Conventional silicon breast implant augmentation mammaplasty (referring to FIG. 1) usually is performed by slitting an incision 100 at the armpit 10, or an incision 110 below the breast 11, or an incision 120 below the areola 12, then inserting a breast implant through the incision 100, 110 or 120 below the breast 11 to augment the breast. During such an operation some problems and difficulties occur, notably:

1. The silicon breast implant is quite bulky and difficult to be inserted manually through the incision 100, 110 or 120. The tissues around the incision 100, 110 and 120 easily become rotten and incision enlarged. Scar is hence easily formed and noticeable after operation.
2. The silicon breast implant is inserted forcefully by fingers through the incision 100, 110 or 120, and is possibly damaged. After a period of time the silicon breast implant could be leaking or disrupted to make the breast hardened or deformed, and result in operation failure.
3. By pushing forcefully the silicon breast implant through the incision 100, 110 or 120 with fingers surgeon's fingers could be hurt.
4. To implant the silicon breast implant through the incision 100, 110 or 120 by pushing with fingers, operation time is longer and results in unfavorable condition to patients.

To remedy the aforesaid problems, many techniques have been developed to make augmentation mammaplasty easier and more efficient. FIG. 2 illustrates a breast implant injector disclosed in U.S. Pat. No. 4,955,906. The breast implant injector 20 includes a hollow tube 21 and a bag 22. The tube 21 has a conical opening 212 at one end 211 which holds the bag 22 inside and beyond. The bag 22 has one end coupled with a slide element 221 which is slidable on the surface of the tube 21. There is a locking ring 23 located on an outer side of the tube 21 at the contact location of a nozzle 201 of the injector 20 and the bag 22. It aims to push a breast implant 24 into the body of a patient. But in practice it still has some drawbacks, notably:

1. The conical opening 212 can only be in inserted in a very shallow location at the incision site rather than in a proper depth. Unless the incision is made larger for the conical opening insertion deeper, the breast implant 24 cannot be inserted deeply inside from the incision and into the submammary pocket, thus the implanted breast implant 24 will easily loosens off after insertion. So that it does not provide much benefits to the operation.
2. The conical opening 212 and the one end 211 of the tube 21 are joined at a location where an unsmooth angular corner 2111 is formed. The angular corner 2111 creates a greater friction to the breast implant 24 and makes pushing out of the breast implant 24 through conical opening 212 difficult.
3. During pushing of the breast implant 24 the outer side of the bag 22 has to be pulled downwards toward the nozzle 201 by the injector 20 (referring to the arrow shown in FIG. 2). A great friction and resistance takes place while the bag 22 is located at the conical opening 212. Adding the resistance caused by the angular corner 2111, the bag 22 could be broken, and pushing out of the breast implant 24 is even more difficult.

Due to the aforesaid injector 20 encounters such a greater resistance during pushing and the breast implant 24 easily slips out during surgery, a disposable implant injector was developed (referring to U.S. Pat. No. 5,201,779 shown in FIGS. 3 and 4A) that has an injection opening expandable automatically. It includes an injection barrel 30. However it also has its own practical problems as follow:

1. It has a guiding rod 31 which is inserted into the injection barrel 30 through a tail end and has a front end extended outside an injection opening 32 where twelve pieces of flaps 33 are being extended first. As the twelve flaps 33 are formed by an injection process, they tend to stick together. Hence they have to be extended first by the front of the guiding rod 31 before they are inserted in the incision of a patient to allow the opening 32 to be disposed inside the incision. Then a plunger 35 with a hard head 351 is pushed forwards through a rear end of the injection barrel 30 as shown in FIG. 4A to inject a breast implant 34 through the opening 32 into a inner side of the breast of the patient for positioning. While the breast implant 34 is pushed and passes through the opening 32, the twelve flaps 33 are pushed by the breast prosthesis 34 to extend outward and form gaps among them. The breast implant 34 thus tends to be wedged in these gaps and damaged during it's being pushed to pass through the opening 32 (referring to FIG. 4B).
2. The injection barrel 30 gradually forms a tapered portion at the bottom of the opening 32 adjacent to the twelve flaps 33. Unsmooth angular corners 301 and 302 are formed at the junction that become obstacles during pushing of the breast implant 34 by the hard head 351 of the plunger 35 in the injection barrel 30. The breast implant 34 cannot be moved smoothly and clogging could occur. When the breast implant 34 reaches the angular corner 301 at the top end of the barrel and the bottom end of the angular corner 302, a greater resistance force is formed. As a result moving of the breast implant 34 is difficult.
3. Because of the inadequate design of twelve flaps 33, an extra element of the guiding rod 31 has to be provided. More unnecessary surgical procedure is needed because of this situation.

SUMMARY OF THE INVENTION

Therefore the primary object of the present invention is to provide a silicon breast implant injector that can easily and safely insert a silicon breast implant into the submammary pocket to facilitate augmentation mammaplasty and enhance implant safety.

The silicon breast implant injector aims to facilitate the silicon breast implant to be quickly passed into the submammary pocket to augment the breast. The injector can shorten surgery time, reduce incision wound damage and scar formation caused by forcefully squeezing the silicon breast implant through a small incision and decreases the finger hurting of the surgeon. Leakage or disruption of the silicon breast implant after surgery also is less likely to occur. The implant injector of the invention includes a hollow tube and a plunger.

The hollow tube has a cylindrical barrel at one end. The barrel has one end tapered to form a first arched barrel to connect an inverse second arched barrel. The second arched barrel is connected to an ejection opening of the same diameter but formed into a short length tube.

The plunger has at least one thrust disk at one end formed at a diameter slightly smaller than the inner diameter of the barrel. The thrust disk has a groove formed on the perimeter to be wedged by a pliable padding ring that is formed at a diameter substantially equal to the inner diameter of the barrel. The plunger has a push rod at another end.

The first arched barrel and the second arched barrel form a smooth connection to reduce push resistance. When in use, a silicon breast implant is disposed in the barrel and pushed by the plunger through the ejection opening. The silicon breast implant is coated with a lubricating fluid non-irritating to human body, thus can be easily and safely pushed and passed into the sub-mammary pocket. As a result, augmentation mammaplasty can be performed rapidly and safely.

By means of the construction set forth above, the invention can provide the following effects and benefits:

1. The implant injector of the invention has the first arched barrel tapered at one end to connect an inverse second arched barrel to form a smooth junction. Hence the silicon breast implant disposed in the barrel and pushed by the plunger can be quickly and safely ejected through the ejection opening and the wound incision into the submammary pocket to augment the breast.

2. The smooth junction of the first arched barrel and the inverse second arched barrel at one end of the barrel can reduce resistance. Hence during inserting the silicon breast implant coated with non-irritating lubricating fluid, disposed through one end of the first arched barrel, the silicon breast implant can be pushed forwards easily by the plunger through the ejection opening at the front end and the wound incision into the submammary pocket to augment the breast.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
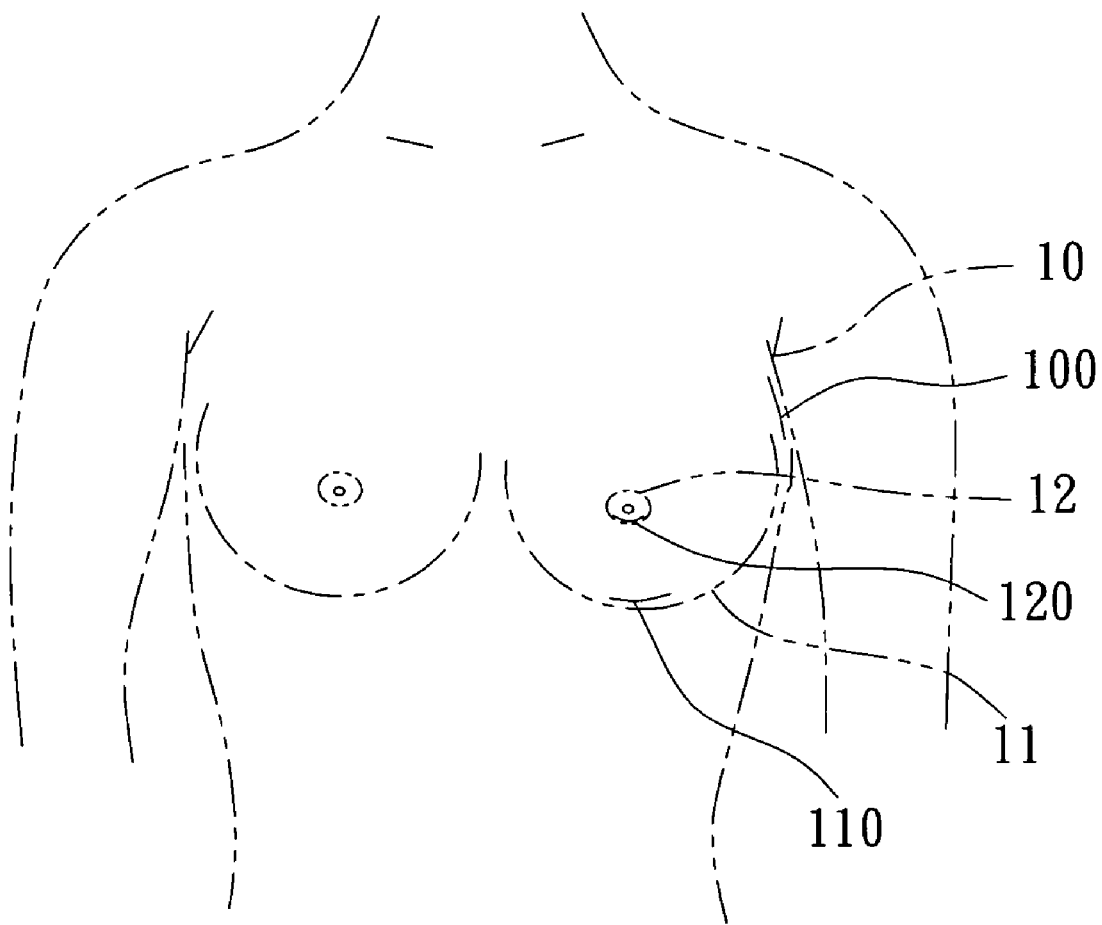
FIG. 1 is a schematic view of a conventional augmentation mammaplasty with incisions formed at three different locations.
Figure 2:
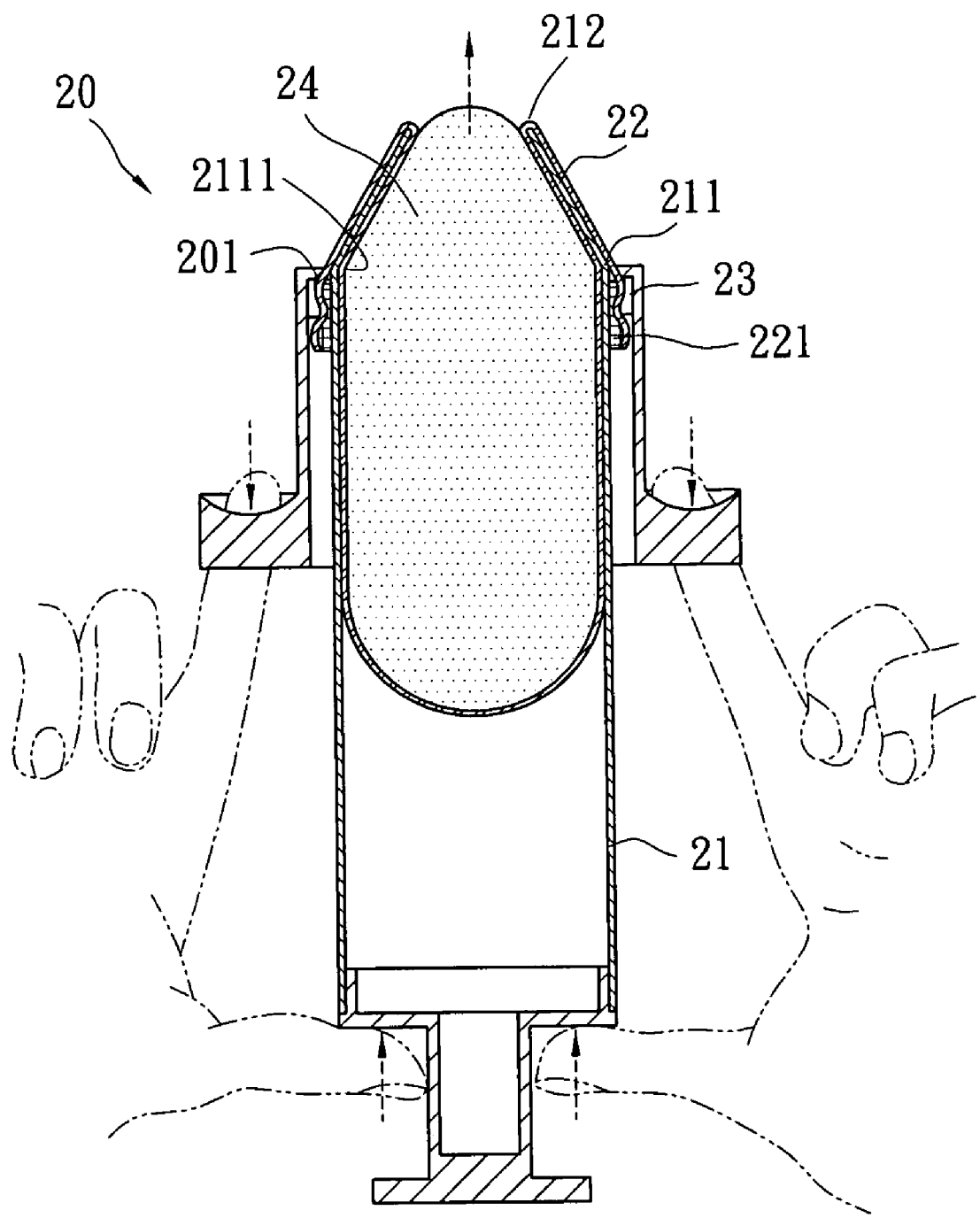
FIG. 2 is a sectional view of a conventional breast implant injector.
Figure 3:
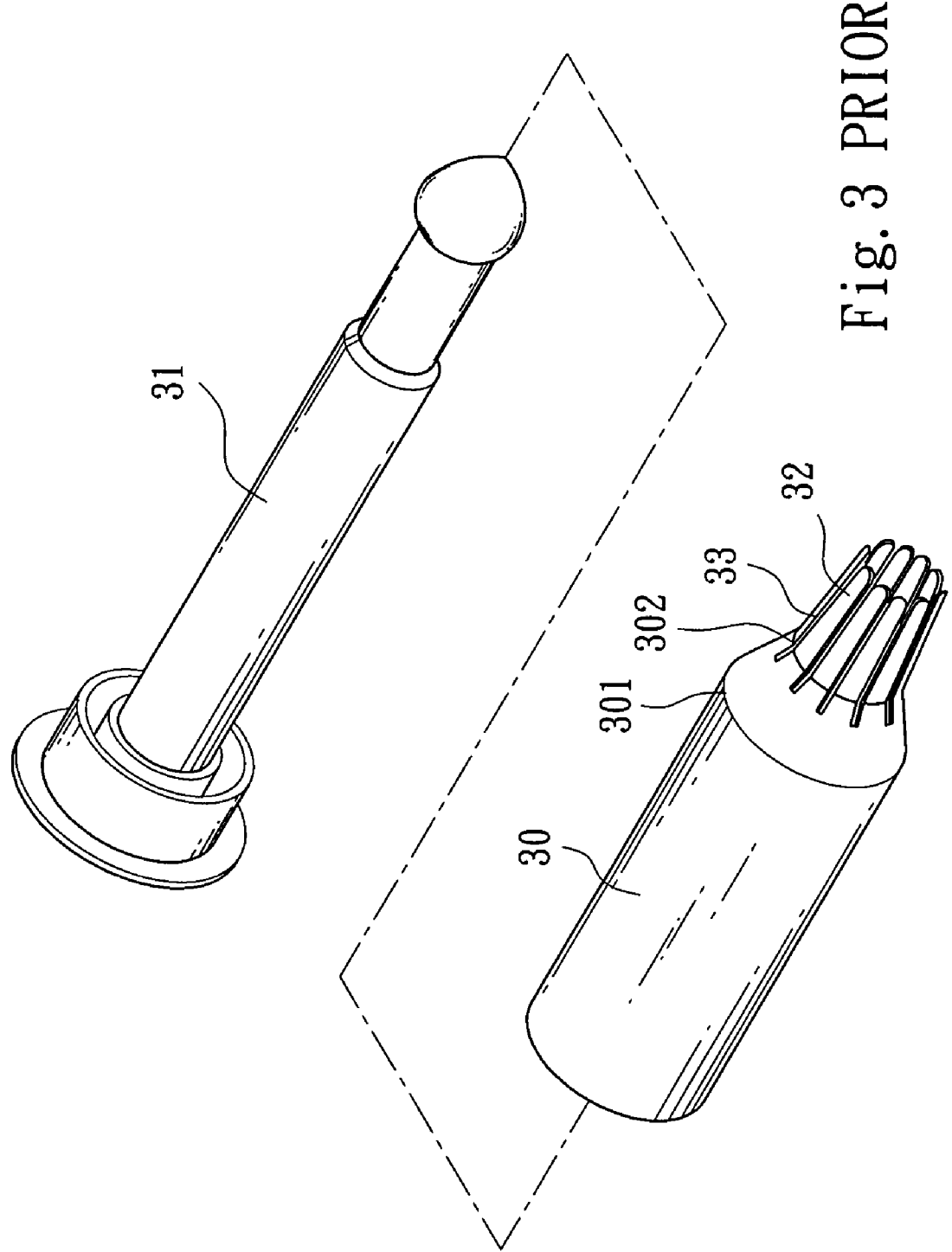
FIG. 3 is an exploded view of a conventional disposable breast implant injector.
Figure 4A:
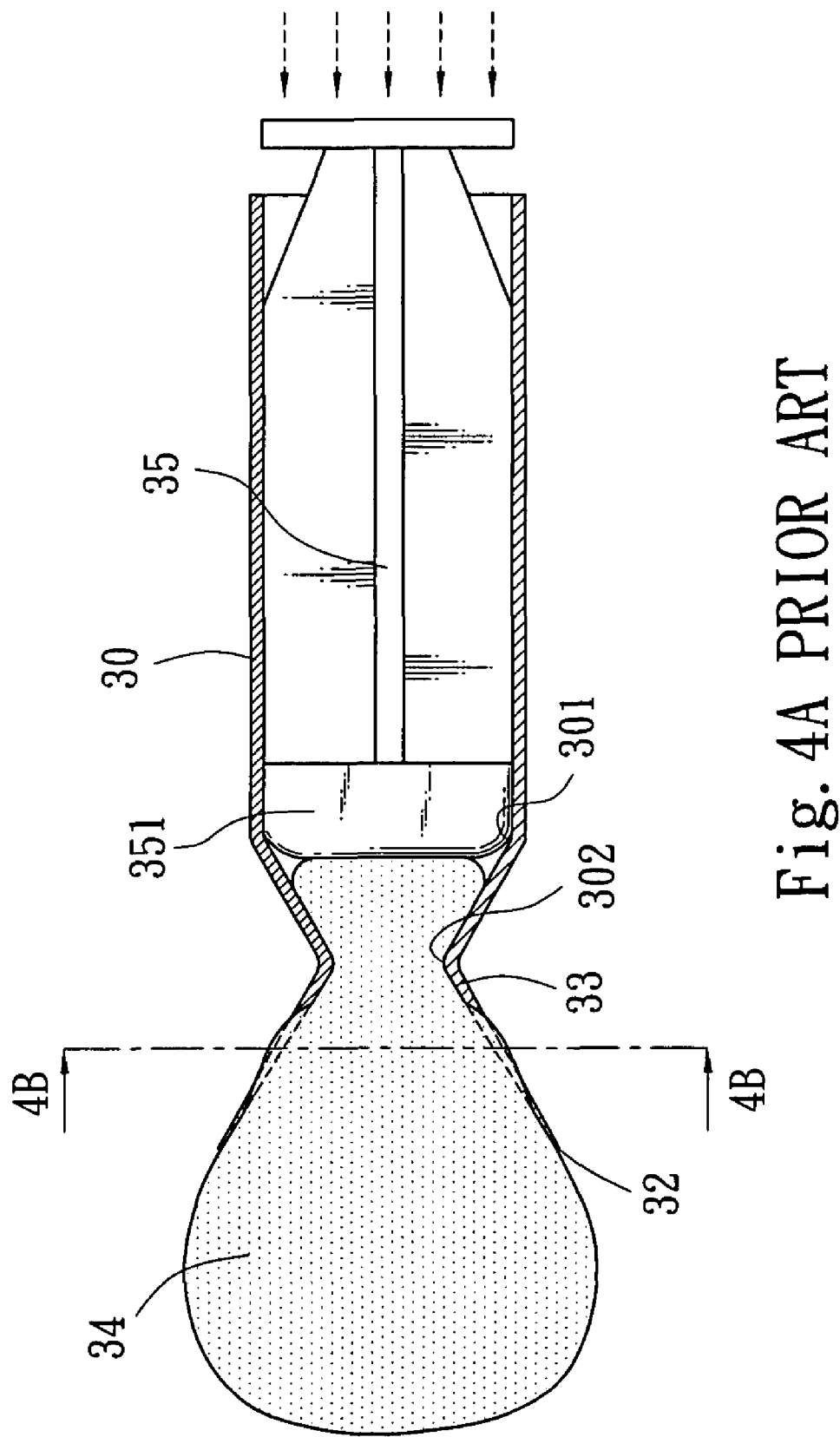
FIG. 4A is a schematic view according to FIG. 3 with a breast implant in a pushing condition.
Figure 4B:
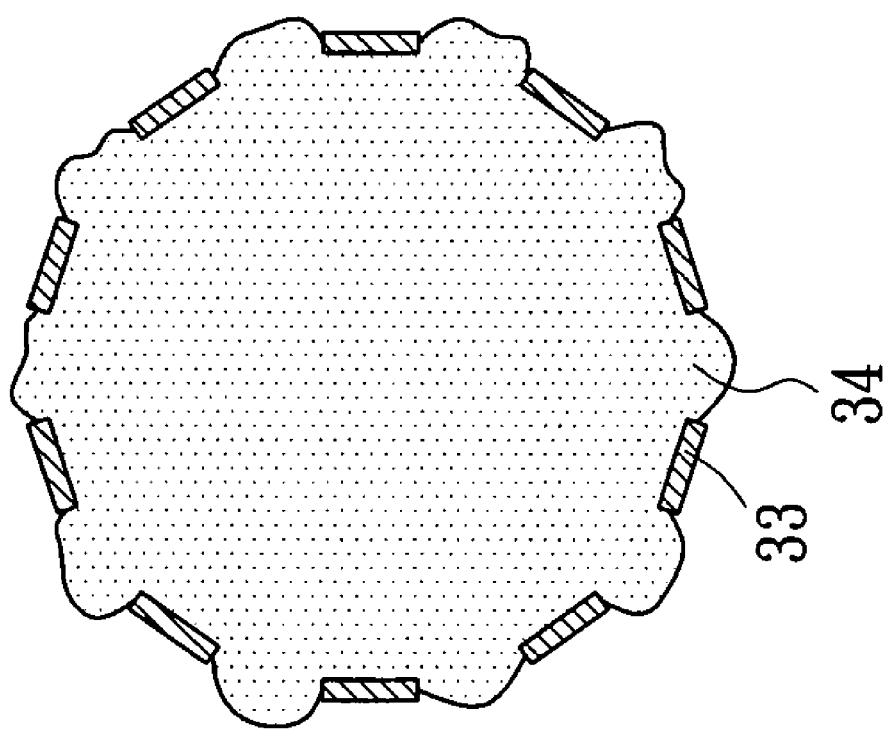
FIG. 4B is a cross section taken on line 4B-4B in FIG. 4A.
Figure 5:
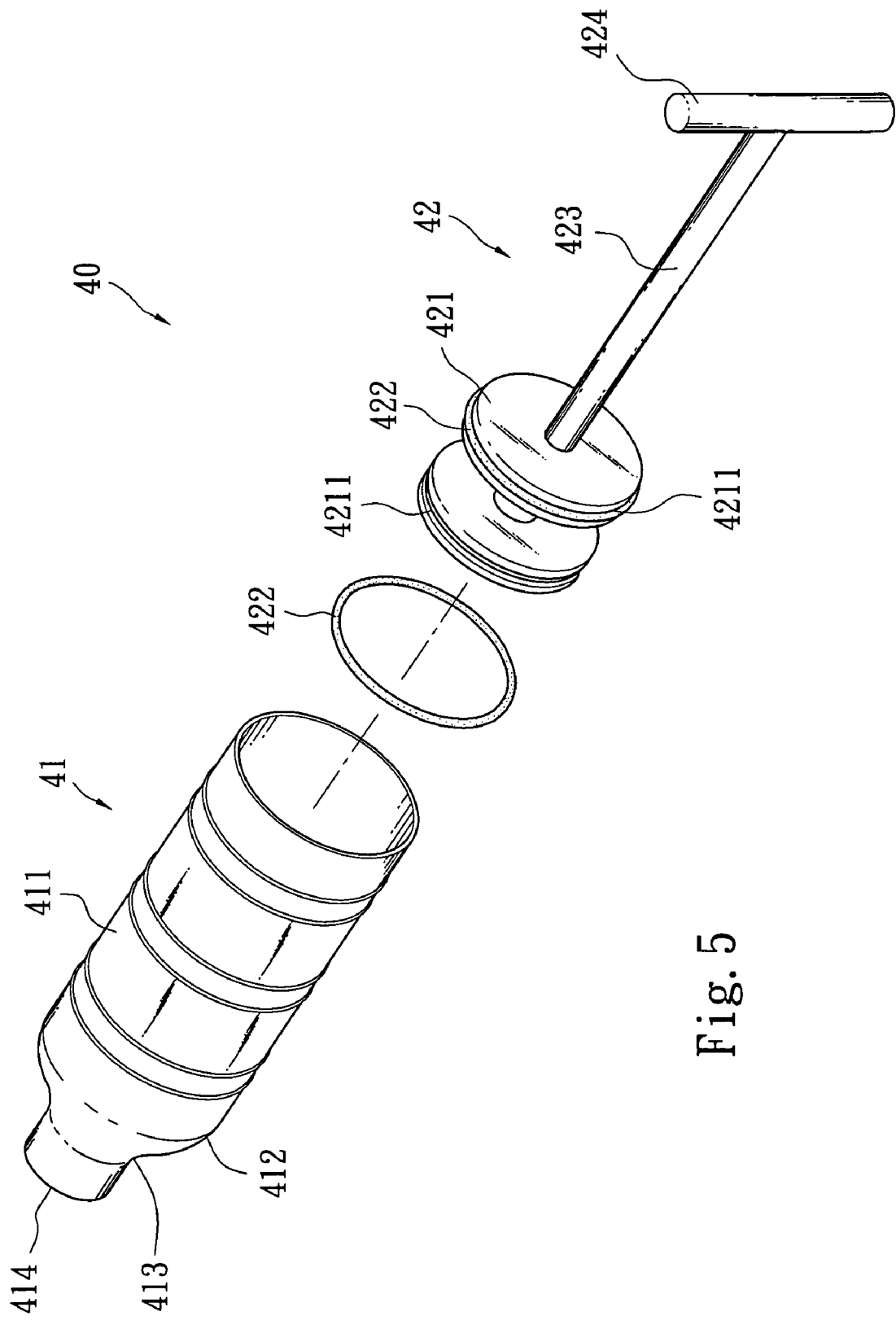
FIG. 5 is an exploded view of the invention.
Figure 6:
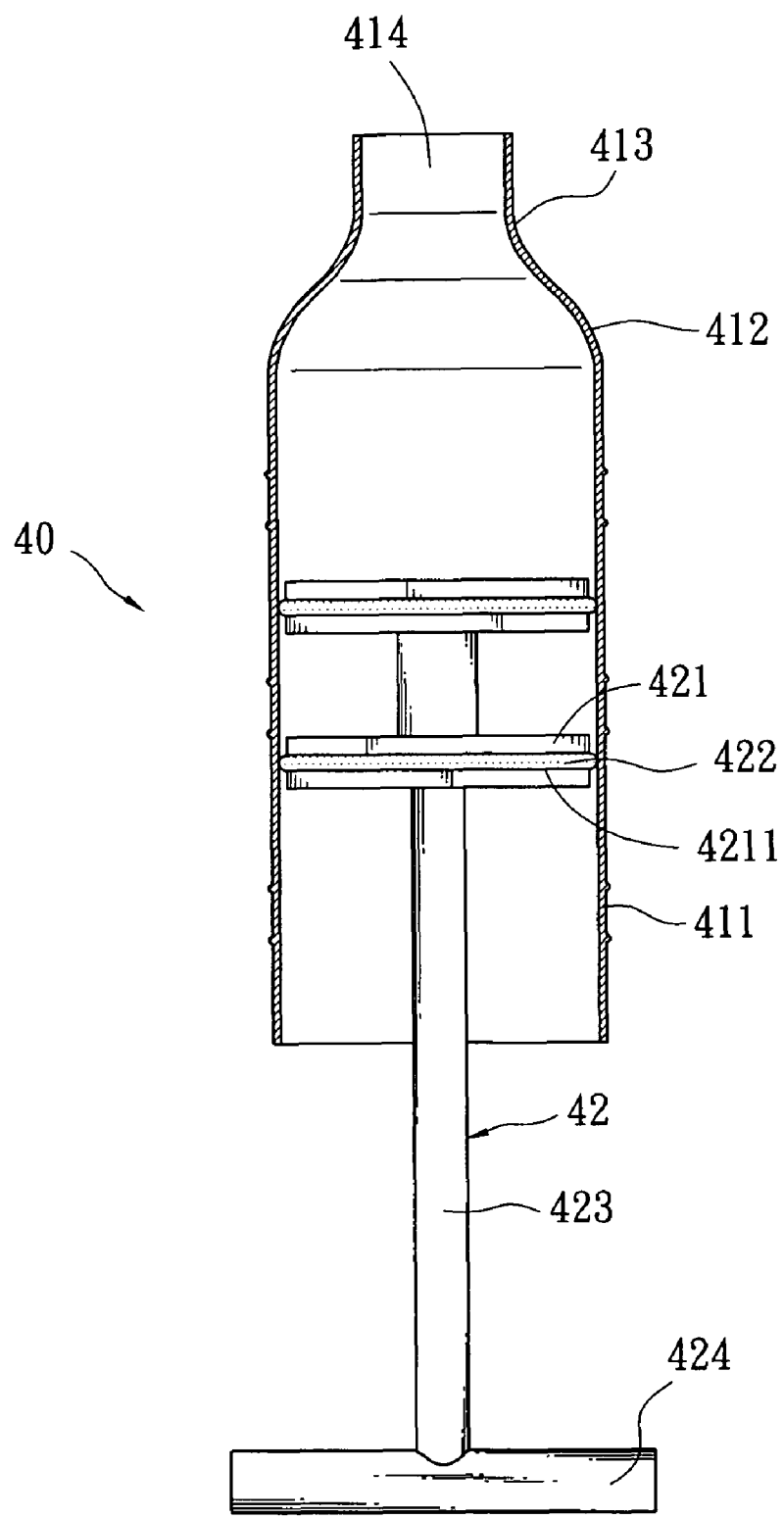
FIG. 6 is a sectional view of the invention showing a plunger held in a hollow tube.

Please refer to FIGS. 5 and 6 for an embodiment of a silicon breast implant injector 40 of the invention, It aims to facilitate the silicon breast implant 51 to be quickly and safely inserted at submammary pocket without being damaged, and enhance implant safety. The silicon breast implant injector 40 includes a hollow tube 41 and a plunger 42.

The hollow tube 41 has a cylindrical barrel 411. The barrel 411 has one end tapered to form a first arched barrel 412 to connect an inverse second arched barrel 413. The second arched barrel 413 is connected to an ejection opening 414 of the same diameter but formed into a short length tube.

The plunger 42 has at least one flattened and circular thrust disk 421 at one end formed at a diameter slightly smaller than the inner diameter of the barrel 411. The thrust disk 421 has a groove 4211 formed on the perimeter to be wedged by a pliable padding ring 422 that is formed at a diameter substantially equal to the inner diameter of the barrel 411. Through the pliable padding ring 422 the thrust disk 421 can be smoothly pushed and moved in the barrel 411. The plunger 42 has a push rod 423 at another end.

The first arched barrel 412 and the second arched barrel 413 are connected at a junction formed at a rather large arc. When in use, the silicon breast implant 51 is coated with a lubricating fluid non-irritating to human body to aid moving.

Referring to FIG. 5, the push rod 423 has a distal end fastened to a vertical thrust rod 424.

Figure 9:
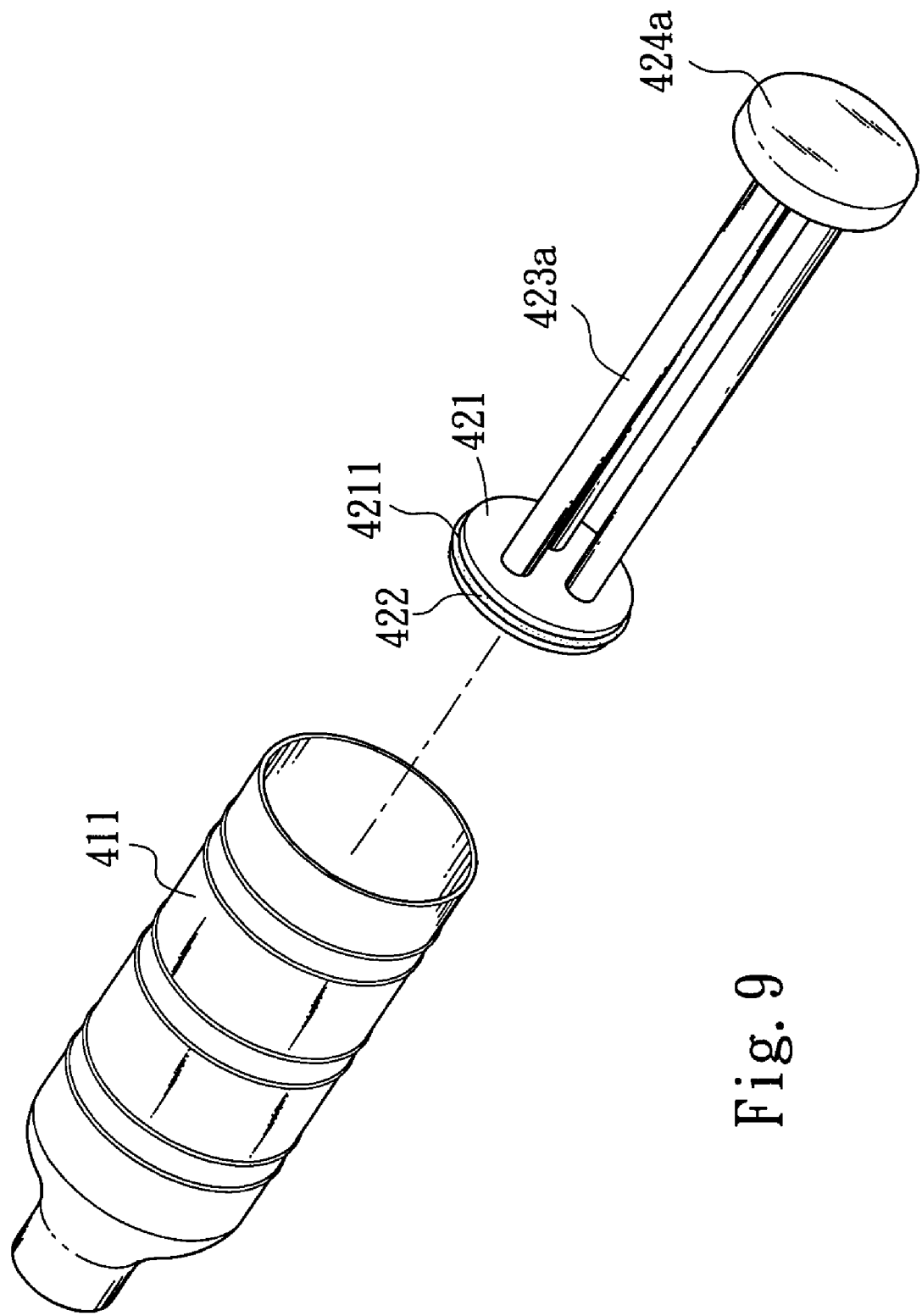
FIG. 9 is an exploded view of another embodiment of the plunger of the invention.
Figure 10:
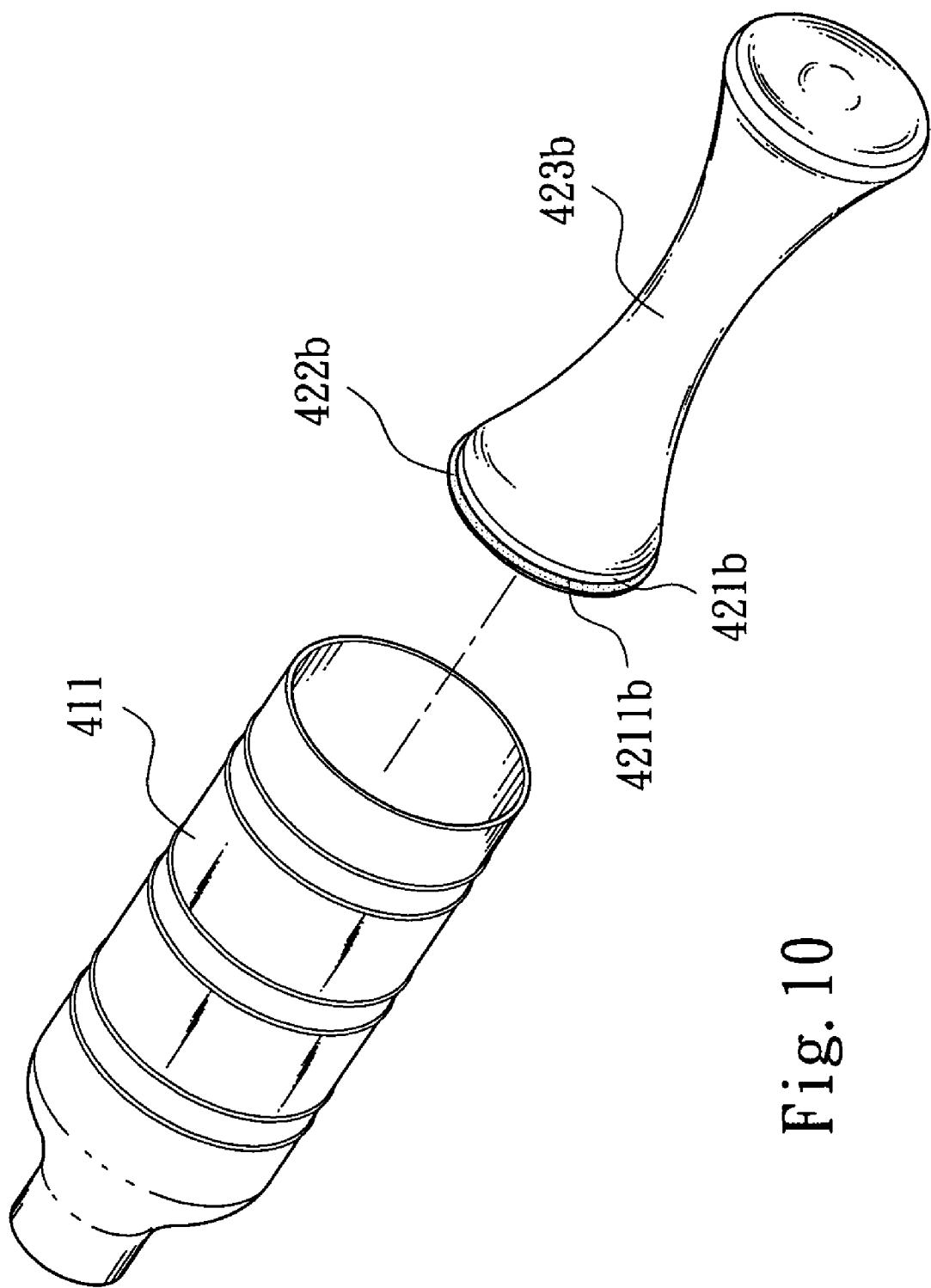
FIG. 10 is an exploded view of yet another embodiment of the plunger of the invention.

Refer to FIG. 9 for another embodiment of the plunger. The thrust disk 421 in this embodiment is fastened to three or more push rods 423a which have distal ends fastened to a vertical thrust disk 424a. FIG. 10 illustrates yet another embodiment in which the plunger has a conical hand grip 423b to facilitate grasping. The conical hand grip 423b has one end forming a thrust head 421b at a diameter slightly smaller than the inner diameter of the barrel 411. The thrust head 421b also has a groove 4211b to be wedged by a pliable padding ring 422b to facilitate steady moving in the barrel 411.

Figure 11:
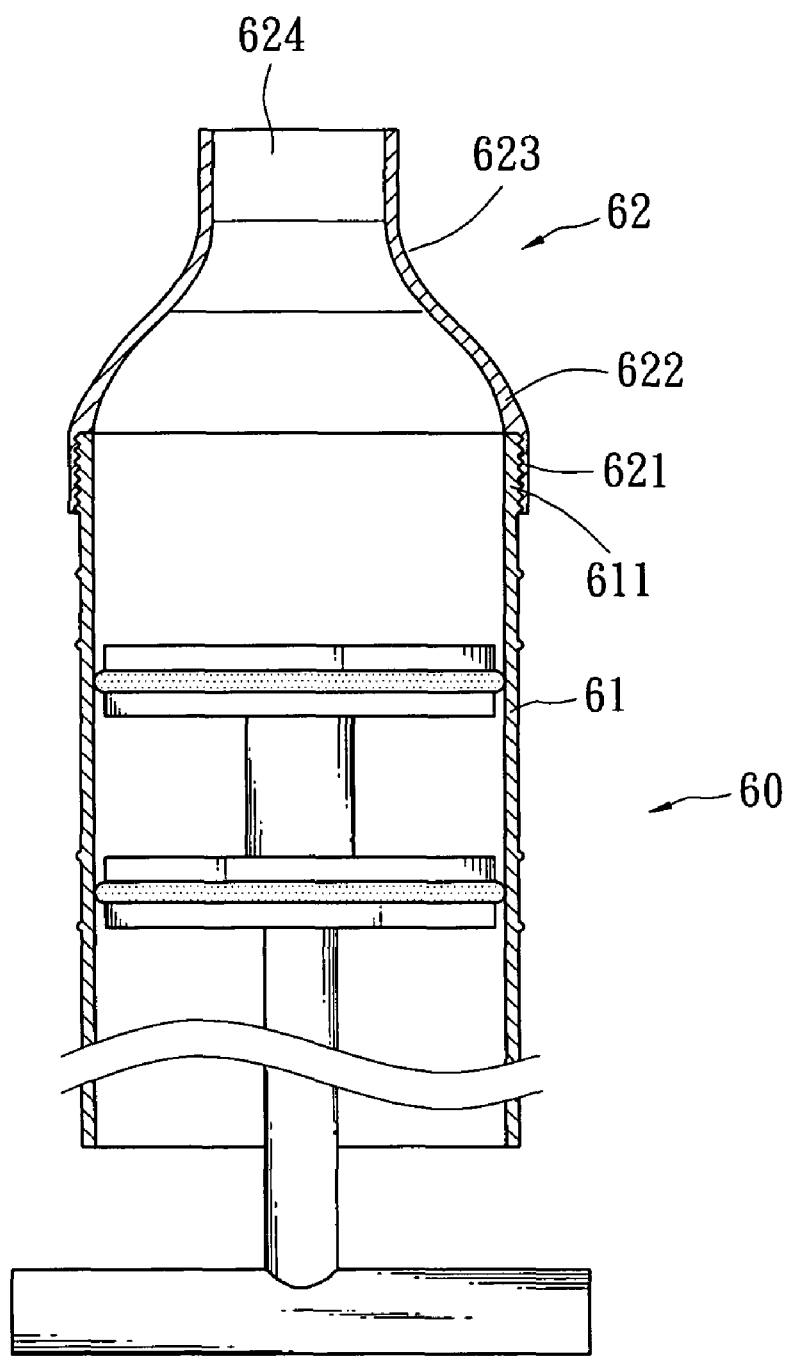
FIG. 11 is a sectional view of another embodiment of the hollow tube of the invention.

Referring to FIG. 11 for another embodiment of the hollow tube 41. It has a barrel 60 formed with screw threads. The barrel 60 includes a barrel body 61 and a cap 62. The barrel body 61 is hollow and has one end formed with external screw threads 611. The cap 62 has one end formed with internal screw threads 621 engageable with the external screw threads 611. The cap 62 has another end tapered to form a first arched barrel 622 and an inverse second arched barrel 623 that are connected together. The second arched barrel 623 is connected to an ejection opening 624 formed at the same diameter but into a short length tube to communicate with the barrel body 61.

Figure 7:
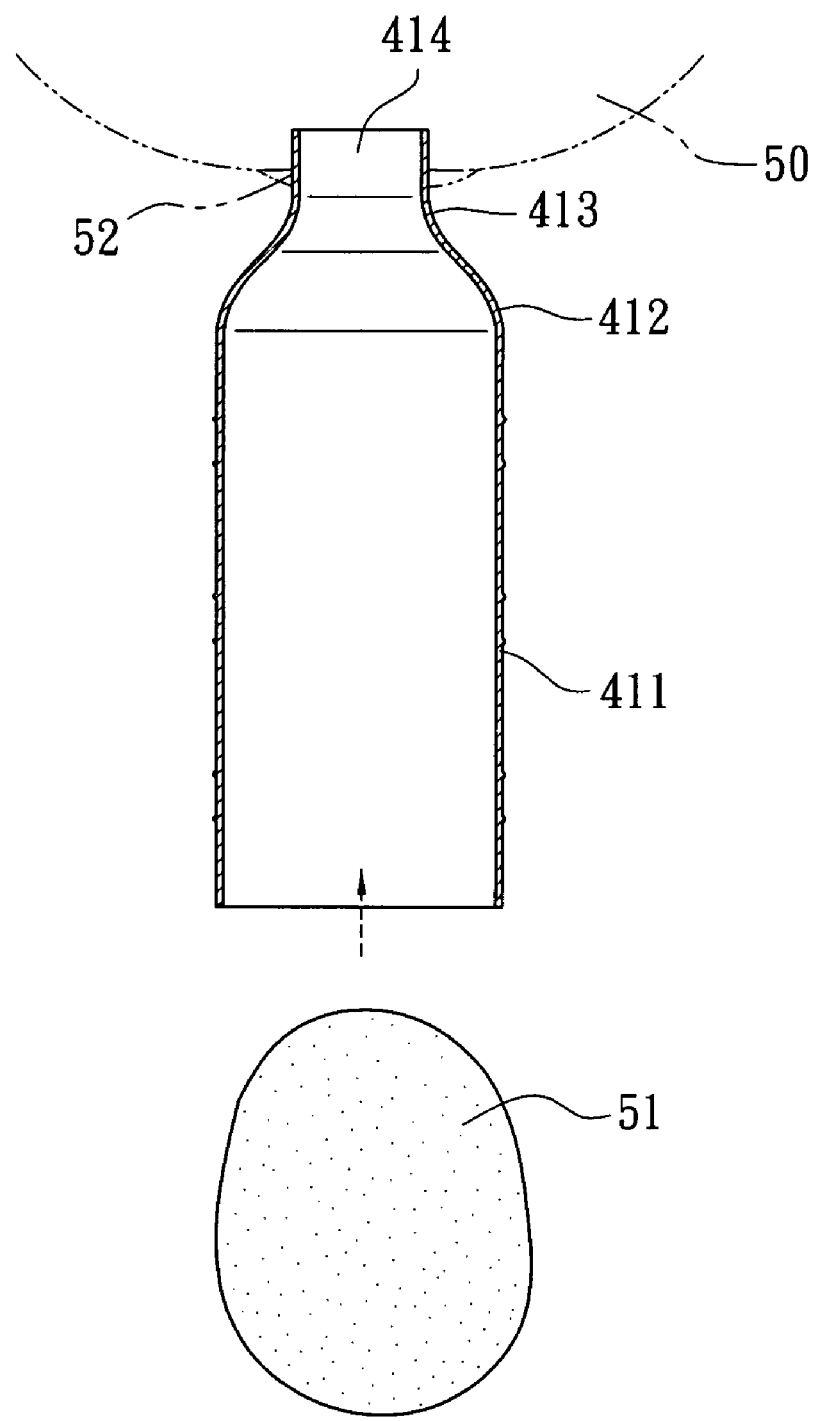
FIG. 7 is a schematic view of the invention for disposing a breast implant into a hollow tube.
Figure 8:
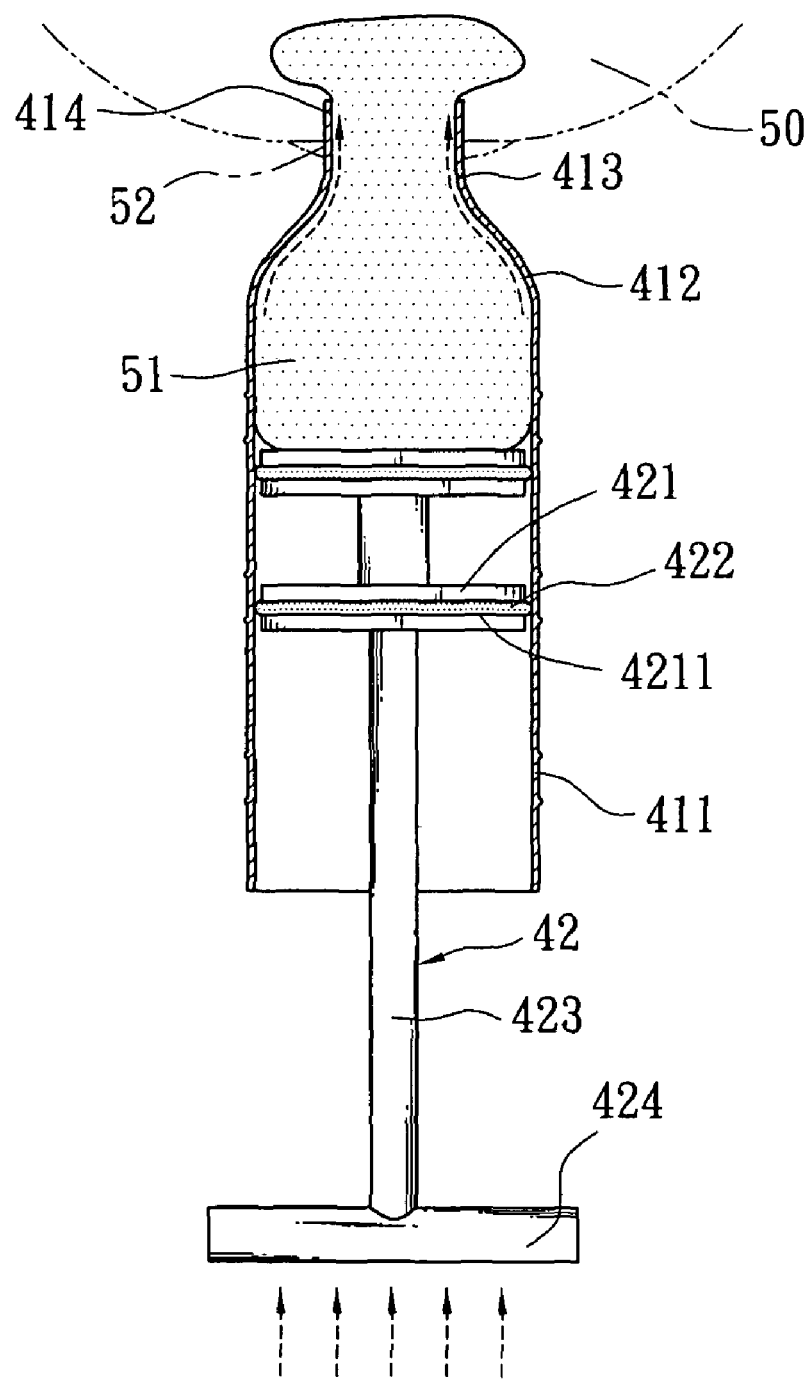
FIG. 8 is a schematic view of the invention showing a breast implant being pushed through an ejection opening to an incision of a breast.

When the invention is in use for implanting the silicon breast implant 51, referring to FIGS. 7 and 8, by means of the construction that has the first arched barrel 412 connecting to the inverse second arched barrel 413, and the second arched barrel 413 connecting to the shorter ejection opening 414 of the same diameter, the ejection opening 414 at the front end of the hollow tube 41 can be fully inserted into an incision 52 of a patient's breast. The silicon breast implant 51 coated with a lubricating fluid non-irritating to human body is placed through one end of the first arched barrel 412, and pushed by the thrust disk 421 of the plunger 42 that has the pliable padding ring 422 forming a close contact with the inner wall of the barrel 411 so that pushing of the plunger against the silicon breast implant 51 can be done steadily and smoothly towards the second arched barrel 413. As the junction of the first and second arched barrels 412 and 413 is a rather large arc, the silicon breast implant 51 coated with lubricating fluid can be ejected out through the ejection opening 414 and incision 52 easily (the incision in this embodiment is formed at the areola, but also may be formed at the armpit or at the lower side of the breast) into the submammary pocket to augment the breast 50. The silicon breast implant injector 40 thus constructed can shorten surgery time, reduce incision wound damage and scar formation that occur to the conventional techniques by forcefully squeezing the breast implant 51 through the small incision. The operation time of pushing the breast implant 51 by surgeon's hands and the possibility of finger hurting that might otherwise occur also can be decreased. Moreover, the breast implant 51 is less likely to be damaged during the pushing process. And the possibility of leakage or disruption of the breast implant 51 after surgery also decreases.

As a conclusion, by forming a smooth connecting junction between the first arched barrel 412 and second arched barrel 412 of the hollow tube 41, pushing resistance decreases. Through pushing of the plunger 42 in the hollow tube 41 the silicon breast implant 51 can be easily and safely passed into the submammary pocket to augment the breast 50. Thus augmentation mammaplasty can be performed more easily and safely.

What is claimed is:

1. A silicon breast implant injector system for augmentation mammaplasty, comprising:
    a silicon breast implant injector, comprising:
        a hollow tube having one tapered end comprising a first convexly curved barrel portion, a second concave curved barrel portion, a curved transition portion connecting to the first and second barrel portions and a third short length tube which connects to the second concave curved barrel portion and comprises a solid cylindrical wall with a distal opening; and
        a plunger, having at least one thrust disk, at least one pushrod and a thrust portion,
        wherein the at least one thrust disk has a diameter slightly smaller than the inner diameter of the hollow tube, wherein the at least one thrust disk is disposed at one end of the at least one push rod, and the thrust portion is attached to and is oriented perpendicular to an opposite end of the at least one push rod, the at least one push rod wherein is disposed between the at least one thrust disk and the thrust portion;
    a silicon breast implant; and
        wherein the plunger is configured to push the silicon breast implant and the implant is capable of being pushed and slid within the hollow tube.

2. The silicon breast implant injector system of claim 1, wherein the hollow tube has screw threads formed thereon and includes a barrel body and a cap.

3. The silicon breast implant injector system of claim 2, wherein the barrel body is hollow and has external screw threads at one end, the cap has internal screw threads at one end to engage with the external screw threads and one tapered end comprising the first convexly curved barrel portion, the second concave curved barrel portion, the transition portion and the third short length tube.

4. The silicon breast implant injector system of claim 1, wherein the thrust portion is a thrust rod or plate.

5. The silicon breast implant injector system of claim 1, wherein the at least one push rod includes a plurality of push rods.

* * * * *